United States Patent [19]

Fish et al.

[11] 4,372,974

[45] * Feb. 8, 1983

[54] ANTICONVULSIVE COMPOSITIONS AND METHOD OF TREATING CONVULSIVE DISORDERS

[75] Inventors: Irving Fish, Tenafly, N.J.; Stephen A. Schwartz, Bronx; Stanley Samuels, White Plains, both of N.Y.

[73] Assignee: New York University, New York, N.Y.

[ * ] Notice: The portion of the term of this patent subsequent to Mar. 30, 1999, has been disclaimed.

[21] Appl. No.: 269,629

[22] Filed: Jun. 2, 1981

Related U.S. Application Data

[63] Continuation-in-part of Ser. No. 162,907, Jun. 25, 1980, Pat. No. 4,322,440.

[51] Int. Cl.$^3$ .................................... A61K 31/195
[52] U.S. Cl. ................................................ 424/319
[58] Field of Search .......................................... 424/319

[56] References Cited

U.S. PATENT DOCUMENTS 3,960,927  6/1976  Metcalf et al. ....................... 424/319

OTHER PUBLICATIONS

Chem. Abst., 47, 2761e (1953).
Comptes Rendus Hebdomadaires des Seances, pp. 1980-1981 (1952).
Ricerca Scientifica (1961), pp. 312-318.
Biochem. Biophys. Research Comm. (1970), pp. 135-141.
Biochem. Biophysica Acta., (1952), pp. 288-289.
Tsuchiya, J. Physio. Soc. Japan, 22-pp. 70-74 (1960).
Meldrum, The Lancet., 8-5-78, pp. 304-306.
Ferrandes et al., Biochem. Pharmacology, vol. 23, pp. 3363-3376 (1974).
Kobrin et al., J. Pharmacology & Exper. Therapeutics, vol. 154, No. 3, (1966) pp. 646-651.
Baxter et al., J. of Biol. Chem., vol. 233, p. 1135 (1938).

*Primary Examiner*—Stanley J. Friedman
*Attorney, Agent, or Firm*—Darby & Darby

[57] ABSTRACT

An orally administered pharmaceutical formulation comprising a solid dosage form containing an aliphatic amino acid compound in which the carboxylic acid and primary amine are separated by three or four units. Administered in an acid pH range, the formulation is useful in the treatment of convulsive disorders and also has anxiolytic and sedative properties.

38 Claims, No Drawings

ANTICONVULSIVE COMPOSITIONS AND METHOD OF TREATING CONVULSIVE DISORDERS

This is a continuation-in-part of our application Ser. No. 162,907, filed June 25, 1980, now U.S. Pat. No. 4,322,440.

BACKGROUND OF THE INVENTION

1. Field of the Invention

This invention relates to a group of pharmaceutically acceptable amino-carboxylic acids and their amide derivatives and to pharmaceutical uses for these compounds. More particularly the invention pertains to the use of these compounds as anticonvulsant, sedative and anxiolytic agents in mammals.

2. Description of the Prior Art

Certain induced, recurrent, generalized seizures in mammals can be prevented by the administration of glutamine (GLN). These seizures have been thought to be related to the depletion of brain glutamine and its product gamma-amino-butyric acid (GABA), which is known to be a major inhibitory neurotransmitter substance acting between the nerve cells in the brain. Decreased GABA in the brain causes seizures. A precursor of GABA is the amino acid glutamine. GABA itself cannot be used clinically to prevent seizures because it does not cross the blood-brain barrier and has serious side effects (hypotension, shock, mortality). Glutamine is metabolized too quickly to be pharmacologically effective.

Several investigators have indicated that the use of GABA agonists given systemically is not associated with a useful anti-convulsant effect. For example, Meldrum (in an article published in The Lancet, Aug. 5, 1978, at p. 304–306) teaches that diffuse activation of GABA receptors by GABA or a GABA agonist given systemically does not provide a useful anticonvulsant effect. An article by Tsuchiya et. al., in Journal of the Physiological Society of Japan, 22,70–74 (1960) reports on the intraperitoneal administration to mice of GABA and delta-amino valeric acid (DAVA) in Tyrodes solution buffered at pH 7.4 ten minutes before inducing convulsions by the application of electroconvulsive shock. The reported results clearly demonstrate that as administered by the authors DAVA is ineffective in preventing or inhibiting convulsions. After initial testing the compound was dropped from subsequent anticonvulsant trials as reported in the article.

It has now been unexpectedly discovered contrary to the results obtained by Tsuchiya et al that DAVA has strong anticonvulsant properties, but only when administered in a form and under conditions markedly different from those used by Tsuchiya et al. Those authors used DAVA under conditions which favored a GABA mimetic role (neutral pH, activity within 10 minutes of injection). We have discovered that DAVA works not as a GABAmimetic but by a totally different action, namely "glutamine sparing". It has also been found that DAVA's anticonvulsant activity is delayed after administration. If they are to provide a useful anticonvulsive effect, the active agents of the present invention must be administered at least 30 minutes prior to the onset of a convulsive episode or seizure. It has also been found that the maximum anticonvulsant effect is achieved if the active agents of the invention are orally administered in coated solid dosage form having a pH between about pH 1.8 and 6.0, and preferably between pH 1.8 and pH 4.0. The reason for the decreased efficacy above pH 6.0 is not fully understood.

It has also been surprisingly found that the active amino acid compounds of the invention are particularly useful as anxiolytic agents in mammals when they are orally administered in the form of their acid addition salts.

Accordingly, it is an object of the present invention to provide a method of preventing seizures, and particularly epileptic seizures in mammals.

Another object of the present invention is to provide pharmaceutical dosage forms containing amino acid compositions which are analogs of glutamine, thus making more glutamine available for conversion to GABA.

Still another object of the present invention is to provide solid pharmaceutical formulations comprising an effective amount for inhibiting the onset of seizures of an amino acid composition or an acid addition salt thereof in a coated oral dosage form at a pH between 1.8 and 6.0.

A further object of the present invention is to provide an effective method of administering the anti-convulsant compositions disclosed herein.

A further aspect of the present invention is to provide effective sedative compositions.

These and other aspects of the invention will be apparent from the following description.

Convulsive disorders (e.g. epilepsy, seizures, fits, convulsions) have in common the occurrence of brief episodes. These episodes are associated with loss or disturbance of consciousness. Such episodes are usually but not always associated with characteristic body movements, and sometimes with autonomic hyperactivity. They are generally correlated with abnormal EEG discharges. The etiology of such disorders is varied and includes, e.g., genetic diseases, metabolic dysfunction, tumors and trauma.

The amino acids found to be useful as anti-convulsant and anxiolytic agents in the present invention may be generally described as aliphatic compounds in which the carboxylic acid and primary amine are separated by three or four units constituting a simple or substituted alkane, an ether or thioether, or an amide forming the backbone of a straight or branched chain molecule. The aminocarboxylic acids are either free acids or an amide and/or ester derivative of the acid.

The active compositions of the present invention are represented by the following general formula:

$$\begin{array}{c} H \\ \diagdown \\ \diagup \\ R_1 \end{array} N-CH-Y-Z_n-CH_2-\overset{\overset{\displaystyle O}{\|}}{C} \diagdown R_2$$

wherein
$R_1$ is H, $$\overset{O}{\underset{\|}{CH_3C-}},\ \overset{O}{\underset{\|}{CH_3CH_2C-}}\ or\ CH_3CH_2CH_2\overset{\overset{\displaystyle O}{\diagup\!\!\!\!/}}{C-}$$

A is H, $CH_3$, $CH_3CH_2-$, $HO-CH_2$, $HO-CH_2CH_2$, $CH_3OCH_2-HS-CH_2-$, $HS-CH_2CH_2-$, $CH_3SCH_2-$,
Y is $C=O$, $HC-OH$ or, $CH-A$,
Z is $CH-A$, O, S; or NH only if Y is $C=O$, and
$R_2$ is $-OH$, $-NH_2$ or $CH_3-CH_2-O-$, n is 0 or 1, and Y is CH—A when n=0; and
A+Y+Z include no more than one Oxygen or Sulfur atom The preferred anti-convulsant of the present invention is DAVA or delta aminovaleric (5-aminopentanoic) acid of the formula:

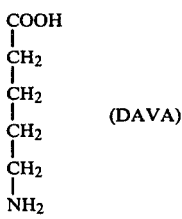

(DAVA)

Aside from its anxiolytic and anticonvulsant activity, DAVA and other compounds of the general formula have been found to posess sedative properties when administered in effective amounts for this purpose.

It has been found desirable to administer DAVA and the other compositions of the invention at a pH of between 1.8 and 6.0. This pH can be achieved by co-administering DAVA or DALA with a pharmaceutically acceptable buffering agent, e.g. organic or inorganic acid, or acid salt. Generally DAVA and the other compounds of the invention are administered in the form of the free acid and preferably in the form of their organic or inorganic acid addition salts. The preferred acid addition salt is DAVA hydrochloride. Additional pharmaceutically acceptable inorganic addition salts useful in the invention include sulfates, phosphates, and carbonates (e.g. DAVA carbonate, DALA phosphate). Illustrative organic acid addition salts of the active ingredients of the present invention include the citrate, lactate, acetate, and fumarate salts (e.g. DAVA citrate).

In considering the substituents of the general formula described above it is noted that only a single oxygen or sulfur atom is present in A, Y and Z. The preferred constituent of the $R_1$ group is hydrogen although acetyl

is also desirable at this position. Besides the $R_1$ groups shown to be useful in the general formula, acyl groups derived from other simple metabolizable organic acids such as, citric, or butyric acid have been found useful.

As constituent A of the general formula hydrogen is the preferred moiety. However, compounds in which A is a $CH_2$—OH group have been found to perform almost as well as those which contain the H moiety.

In addition to the moieties enumerated in the general A formula set forth above, anxiolytic and anticonvulsant activity has also been found in compounds of the general formula wherein the A constituent is selected from groups having homologous side chains with 3 or 4 carbons in a straight or branched chain configuration. Representative of this class of constituents is 5-amino-4 hydroxy octanoic acid.

The preferred constituents of the Y and Z groups is $CH_2$, which is especially preferred. As to the Z groups, it should be noted that NH may only be present at this position when the Y constituent is $>C=O$.

Hydroxy (—OH) is the especially preferred constituent at the $R_2$ position in the general formula for the present pharmaceutical compounds, although amino (—$NH_2$) is also a preferred $R_2$ constitutent. Compounds in which other esters and amides (e.g. peptides) are constituent $R_2$ have shown some anticonvulsant activity, but are not believed to offer any particular benefit or advantage over those in the general formula.

In addition to DAVA, the preferred active agent of the present invention, 5-amino-4-oxo-pentanoic acid, 2-aminoethoxy acetic acid, 2-aminoethylthio acetic acid, and 5-amino-4-hydroxy pentanoic acid, also display anticonvulsant and anxiolytic properties in animals.

Although principal use of the compounds of the invention is anticipated to be as orally administered pharmaceutical agents for prevention, inhibition, and arrest of epileptic discharges in humans, the desirable sedative properties of DAVA are also of great significance. This is particularly true in view of the relatively non-toxic nature of the present compounds and the fact that they may be synthesized at relatively low cost.

The compositions of the present invention are preferably administered in a solid dosage form via the oral route. Although parenteral administration by subcutaneous, intramuscular and intravenous injection is also effective, the improved efficacy obtained at low pH makes this a less desirable route of administration in large mammals as it causes local irritation at the administration site and can lead to erythruria. Due to the highly acid pH of the active ingredient it is unsatisfactory to administer it alone via the oral route. The active ingredient in the oral dose preferably is administered in the form of a coated tablet, pill, beadlet, capsule, or other solid dosage unit. The coating or protective capsule is required to prevent the highly acid active ingredients from damaging the delicate tissues of the buccal cavity or the pharynx during administration. Suitable coatings may be prepared from an aqueous suspension containing sugar and insoluble powders such as starch, calcium carbonate, talc or titanium dioxide, suspended by means of acacia or gelatin. Waterproofing coatings consisting of substances such as shellac, cellulose acetate phthalate may be applied to a pill or talbet from a nonaqueous solvent and prior to the application of a sugar coat. Film coatings consisting of water soluble or dispersible materials such as hydroxypropylmethylcellulose, methylcellulose, carboxymethylcellulose sodium, and mixtures of cellulose acetate phthalate and polyethylene glycols applied out of nonaqueous solvents are also useful in coating the tablets and pills made according to the invention. Soft shell (gelatin) capsules of the type which do not dissolve until reaching the acidic environment (approximately pH 1.0-3.0) of the stomach are also useful as dosage forms in the invention. However, the capsules may comprise any well known pharmaceutically acceptable material such as gelatin, cellulose derivatives and the like. The active ingredients may be compounded in the desired oral form in combination with inert ingredients including fillers such as talc, lactose, starch, bentonite and diatomaceous earth; lubricants and food flavorings. Tablets for use in the invention may be made by punching or compressing the active ingredients on a tabletting machine.

Liquid oral doses in the form of solutions, and suspensions are also contemplated by the invention as are suppositories for rectal administration. In making solutions and suspensions the active ingredients may be dissolved or suspended in distilled water, conventional U.S.P. syrup formulations or any other pharmaceutically acceptable carrier liquid. For parenteral administration the compounds of the invention are preferably dissolved in distilled water, isotonic saline solution or any other pharmaceutically acceptable carrier liquid.

Several of the (4-) and (5-) amino carboxylic acid compounds in this series are commercially available. They include among others, 5-aminopentanoic acid, 5-aminolevulinic acid, and glycylglycine, all available from Sigma Chemical Company, St. Louis, Mo.

The other compounds of the general formula can be directly prepared by conventional synthetic procedures or using processes described in the literature. Thus, 2-aminoethoxy-acetic acid may be prepared according to the synthesis taught in Academie des Sciences, Paris. *Comptes Rendus Hebdomadaires des Seances* (Compt. Rend.) 234, 1980 (1952), CA 47,2761e. 5-amino-hexanoic acid can be synthesized by the method in *Ricerca Scientifica 1,* IIA, 312 (1961), CA57,9658h. 5-amino-4-hydroxy-pentanoic acid is prepared by reduction of 5-aminolevulinic acid using the procedure taught in *Biochemical Biophysical Research Communications* 39, 135 (1970); and 4-amino-5-hydroxy-pentanoic acid, synthesized by the method in *Biochemica Biophysica Acta* 8, 287 (1952), CA 47, 4843d. Other compounds of the invention such as 2-acetoxy-1-propylamine, 1-acetoxy-2-propylamine, 2-acetoxy-1-butylamine, 1 acetoxy-2 butylamine and 2-amino-ethylthio-acetic acid are prepared by adaptation of the method for preparing 2-amino ethoxyacetic acid (taught in the *Compt. Rend.* article referred to above) by substituting, respectively, in the synthesis of each of the above amino acids: 1-amino-2-propanol, 2-amino-1-propanol, 1-amino-2-butanol, 2-amino-1-butanol and 2-amino-ethylthiol.

It is to be understood that where an amino acid compound described in the art is identical with one of the above specified named compounds, but has been known by another name by reason of isomerization or production in accompaniment with other compounds, the identification of such substances by the name set forth above is intended to identify the same compound under all other designations.

When used as anticonvulsant or sedative agents in mammals, the active agents present compositions are administered at a dosage level of from about 0.03 to about 40 mmol (3.5–4680 mg, and preferably 50–200 mg.) of active ingredient per kilogram of body weight per day. The daily effective dosage, or the dosage required to prevent or inhibit convulsions from a particular disease or stimulus, or to achieve sedation depends upon the condition being treated, the individual characteristics of each mammal being treated and the nature of the physical or chemical stimulus inducing or responsible for the convulsive activity. Thus, the exact dose required to alleviate convulsions attributable to a particular disorder or stimulus, or to their effects will vary within the dosage range, discussed above from one patient to another. The anxiolytic properties of the present compounds are evident in the same dosage ranges employed for anticonvulsant treatment. Sedative properties of the present agents are apparent at the higher end of the dosage levels discussed above (e.g. dosages of between about 10 and 40 mmol active ingredient per kilogram of body weight are sedative dosages). Within the stated dosage ranges, the effective dose for small mammals (e.g. mice) is approximately 10 times the effective dose for larger mammals (e.g. cats, dogs, humans).

Solid pharmaceutical dosage forms such as pills, capsules, and tablets may contain from 5 to about 750 milligrams of active ingredient. Preferably from about 50 to about 500 milligrams of active ingredient is incorporated in each solid dosage form together with the required amount of buffer material if any is required, to bring the pH of the dosage to between pH 1.8 and pH 6.0.

The liquid dosage forms of the present invention are preferably administered in the form of a solution or suspension in a pharmaceutically acceptable vehicle, preferably distilled water. Liquid dosages containing from about 5 to about 100 milligrams of active ingredient per cubic centimeter of vehicle have been found to be useful in administering these agents to mammals. The preferred concentration within this range will depend upon the age and weight of the subject being treated.

It is also contemplated that the anti-convulsant agents of the invention may be administered in the form of rectal suppositories. Suitable suppository dosage forms may be prepared by incorporating the active agent into a shapeable base material. Among the suppository bases that can be used to prepare suppositories according to the present invention are cocoa butter, glycerinated gelatin, hydrogenated vegetable oils, mixtures of polyethylene glycols of various molecular weights, and fatty acid esters of polyethylene glycol. Rectal suppositories for adults are tapered at one end, usually weigh about 2–4 grams and may contain from about 5 to about 500 milligrams of active ingredient. Preferably such suppositories are made from one or more bases having a melting point that will enable them to melt or dissolve slowly upon retention in the rectal cavity.

The anticonvulsant activity of the instant aminocarboxylic acid compounds was measured against seizures produced in female DBA/2J mice using: L-methionine-RS-sulfoximine (MSO), 100 mg/Kg injected subcutaneously (SC), pentylenetetrazole (PTZ), 65 mg/Kg, SC or electroconvulsive shock (ECS), 18 mA at 380 V for 0.1 sec. These are standard test conditions which produce convulsions in 90–100% of saline injected (control) animals. Anticonvulsant activity was also tested using supramaximal ECS which produces tonic extension seizures in 100% of control animals.

In testing representative compounds of the invention for anti-convulsant activity Glycylglycine (Glygly), Glycine (Gly), Glutamine (Gln), 5-amino-valeric acid (DAVA) and 5-amino-levulinic acid (DALA) were administered to the DBA/2J animals SC at 15 mmol/kg body weight or orally at 30 mmol/kg of body weight. The active ingredients were injected or administered 45 minutes after MSO injection or 60 minutes before PTZ or ECS administration. Saline injected controls were treated in parallel with those animals receiving an active dose. In some instances GlyGly injected animals and saline controls were given ECS after 180 minutes.

An important aspect of the present invention involves administration of the active anti-convulsant substantially prior to the application or onset of the convulsive stimulus or attack. Generally the active agent should be administered from at least 30 minutes to 4 hours or more before application or onset of the seizure stimuli whose inhibition is sought. The interval between administration of the agent and observation of its anticonvulsant effect is believed to be attributable to the fact that the mode of action of these agents is to spare glutamine, a GABA precursor, thus making more glutamine available for the production of GABA. During this latency, the glutamine which has been spared must travel to the pre-synaptic terminals of the neurons where it is metabolized to GABA. Glutamine also plays an important role in other metabolic processes in the brain. Thus, the mechanism of action of the active compounds in the present invention is believed to be different than for prior art anticonvulsant agents which directly affect the ability of the synapses to transmit neural impulses.

For administration via the parenteral route in mice, the acid compounds (pH 1.8–6.0, preferably pH 1.8–4.0) of the invention were injected subcutaneously, in isotonic saline solution, at a dose of 15 mmol/Kg body weight. Anti-convulsant activity against seizures produced by MSO or PTZ was determined by measuring the difference in time to onset of seizures between experimentally treated animals and saline injected control animals. The effectiveness against ECS seizures was measured on a four point scale with seizure severity being scored as follows: Seizure with full extension and death, 3; seizure will full extension, 2; clonic seizure without tonic extension, 1; no seizure, 0. Dosage and time data were obtained using supramaximal ECS which produces toxic extension seizures in 100% of control (saline injected) animals.

EXAMPLE I 5-amino-4-hydroxypentanoic acid was prepared according to the following procedure:

222 mg NaBH$_4$ was dissolved in 30 ml 0.1 M NaHCO$_3$. 5 ml of this solution (1000$\mu$ moles of NaBH$_4$) was added to 250$\mu$ moles (32.8 mg) of $\delta$-amino-levulinic acid (5-amino-4-oxo-pentanoic acid) in 5 ml of water. The mixture was stirred at room temperature for about 20 hours. The excess NaBH$_4$ is destroyed by adding HCl dropwise until the pH is 2.

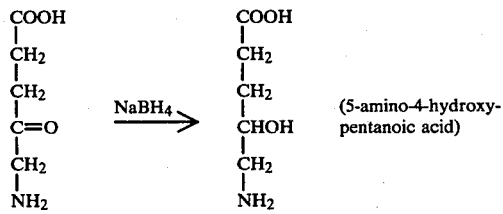

EXAMPLE II $\gamma$amino-$\delta$-hydroxy valeric acid (4-amino-5-hydroxypentanoic acid) was prepared according to the following procedure:

353 mg of $\gamma$-L-glutamylglycine was added to 5 ml absolute ethanol containing 0.11 N HCl (dry gas) and the mixture stirred for a half hour at room temperature. The alcohol was then removed under vacuum and the ethyl ester of the dipeptide was dried under vacuum with P$_2$O$_5$. 174 mg of this product was finely emulsified in 10 ml of N-ethylmorpholine containing 180 mg of lithium aluminum hydride. The mixture was stirred for 8 hrs. under an atmosphere of dry nitrogen at 50° C. The excess hydride was destroyed with a drop of water and the precipitate filtered and washed with ether to remove the morpholine. The precipitate contains almost all of the diol, a yield of about 31%. The precipitate was subjected to Soxhlet extraction for 24 hours with dry ether after acidification with a drop of concentrated H$_2$SO$_4$. This removes the residual N-ethylmorpholine. The peptide diol remaining in the precipitate is hydrolyzed with 6 N HCl at 110° C. for 24 hours in a sealed tube. The residual HCl is evaporated, the solution desalted and the 4-amino-5-hydroxypentanoic acid isolated by [paper] chromatography.

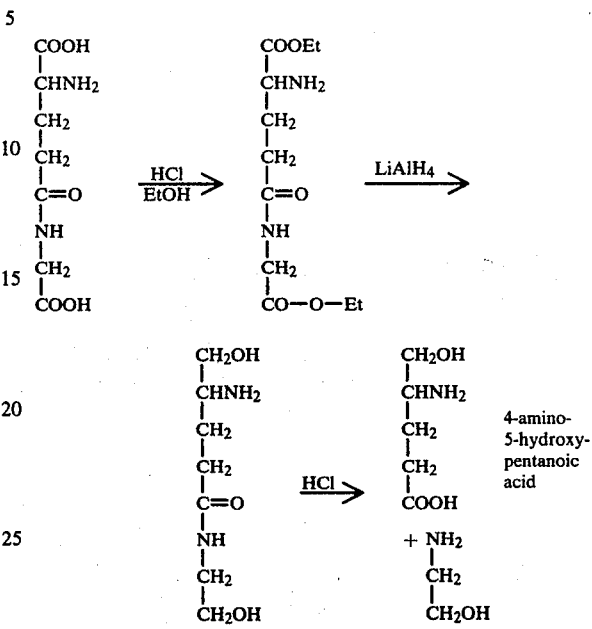

EXAMPLE III

5-Aminohexanoic Acid was prepared by combining 0.5 g 2-methylcyclopentanone and 9.5 ml 2 N NaOH in sufficient ethanol to give a homogeneous solution. The mixture was cooled to 0° C., 0.9 g of benzene sulfohydroxamic acid (C$_6$H$_5$SO$_2$NHOH) was added, and the mixture stored overnight in the refrigerator. Thereafter the mixture was concentrated in vacuo and extracted with ether. The post-extraction residue is brought to between pH 5–6 with 2 N HCl extracted with chloroform to give an oil bp. 70°–80° C. (4 mm), 7–8% yield. This product N-hydroxy-6-methyl-2-piperidone, is reduced with hydrogen over 10% palladium-charcoal to a lactam, 6-methyl-2-piperidone (mp. 79°–80° C.). The lactam is hydrolyzed with aqueous Ba(OH)$_2$ to yield 5-amino-hexanoic acid.

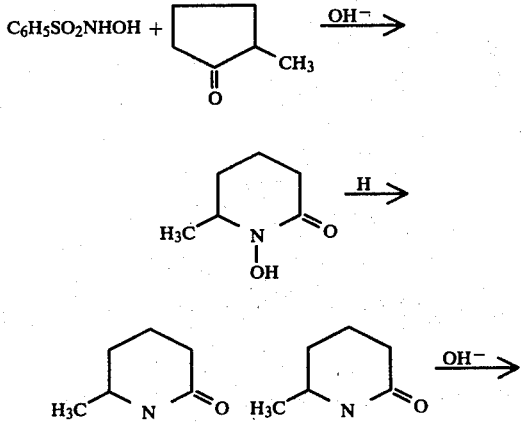

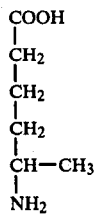

EXAMPLE IV 2-aminoethoxy-acetic acid was prepared by dissolving 35 g of ethanolamine in 100 ml anhydrous dioxane. 11.5 g sodium metal was slowly added in small portions with stirring and heated until fully dissolved. To this solution 63 g of monochloroacetic acid was added dropwise while cooling the mixture. The mixture was then refluxed for 2 hours to precipitate sodium chloride which is filtered off. The dioxane is removed by evaporation. The product, 3-morpholone, is extracted with boiling benzene. Colorless, needle-shaped crystals are obtained which are crystallized in anhydrous ether (mp. 105° C.). An additional quantity of crystals can be obtained by washing the sodium chloride precipitate with boiling ethanol. The total yield is 70%. The lactam is easily hydrolyzed to 2-aminoethoxy acetic acid with aqueous Ba(OH)₂ which is easily crystallized (mp. 182° C.).

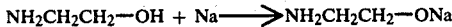
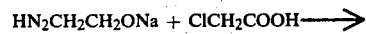
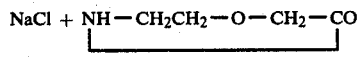
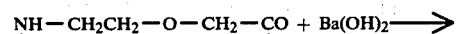
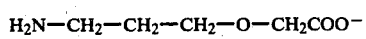

Substitution of other amino alcohols or amino-ethane-thiols can be used to obtain the 4- and 5-methyl substituted compounds or the analogous thio ethers. 2-acetoxy-1-propylamine, 1-acetoxy-2-propylamine, 2-acetoxy-1-butylamine, 1-acetoxy-2 butylamine and 2-amino-ethylthioacetic acid are prepared by adaptation of the method for preparing 2-amino ethoxyacetic acid (taught above) by substituting, respectively, in the synthesis of each of the above amino acids: 1-amino-2-propanol, 2-amino-1-propanol, 1-amino-2-butanol, 2-amino-1-butanol, and 2-amino-ethylthiol.

The following examples illustrate the anti-convulsive, sedative and anxiolytic qualities and the method of administration and compositions of the present invention:

Female DBA/2J mice were injected with normal saline solution, the volume of solution (ml) being equal to 0.01 times the body weight in grams. Either 60 or 180 min. later the animals were attached by ear clips to a conventional laboratory electroshock apparatus which delivered 18 mA at 380 V for 0.1 sec. (constructed according to the principle of Behavioral Research Methods & Instruments, Vol. 4, p. 313, 1972). The severity of seizures was scored using a system where 0 is no seizure, 1 is a clonic seizure, 2 is a seizure with extension, and 3 is a seizure with extension and death.

| | RATING SCALE | | | | Total |
|---|---|---|---|---|---|
| | 0 | 1 | 2 | 3 | No. |
| Saline 60 min. | 1 | 7 | 15 | 3 | 26 |
| Saline 180 min. | 0 | 3 | 5 | 2 | 10 |

A second group of animals were injected subcutaneously with a delta-amino acid of the invention, at a dose of 15 mmoles/kg using a 1.5 M solution in normal saline. These mice were also tested at 60 or 180 minutes using the electroconvulsive shock apparatus. The following results were recorded:

| | Time | Total No. | 0 | 1 | 2 | 3 | Fisher's Exact Probability |
|---|---|---|---|---|---|---|---|
| 5-Aminopentanoic Acid | 60 min. | 25 | 17 | 4 | 4 | 0 | 0.00000202 |
| 5-Aminolevulinic Acid | 60 min. | 10 | 6 | 2 | 2 | 0 | 0.00131 |
| Glycylglycine | 180 min. | 10 | 6 | 2 | 1 | 1 | 0.0108 |

Application of Fisher's Exact Probability test to the results confirmed that the lessened seizure incidence in the treated animals was a statistically valid observation and not a chance occurrence.

EXAMPLE VI

Two groups of DBA/2J female mice were injected subcutaneously with saline (0.01 ml x body weight in grams) or an active compound of the invention (15 mmol/kg of body weight). After 60 min. the animals were injected subcutaneously with the chemical convulsant pentylenetetrazol at a dose of 65 mg/kg body weight. The incidence of seizure activity was observed and recorded for each animal with the following results. Severity was scored by the presence or absence of seizures and the time to onset (latency).

| | Total No. | # Animals Without Seiz. | # Animals With Seiz. | Average Latency Time |
|---|---|---|---|---|
| Saline | 20 | 0 | 20 | 5.6 min. |
| 5-Aminopentanoic acid | 20 | 6 | 14 | 10.7 |

As determined by Fisher's exact probability test (two-tailed), the probability that the six animals without seizures was due to random chance was 0.0202. The probability that the delay of seizures in the drug treated animals was due to random chance, was evaluated by the students t-test and was determined to be $P<0.0001$. This confirms that the results are valid and not chance observations.

EXAMPLE VII

A group of DBA/2J female mice were given a 1.5 M aqueous solution of 5 aminopentanoic acid by stomach tube at a dose of 30 mmoles/kg. of body weight. A group of control animals were given an equivalent volume of water (0.02 ml/g) by the same route. Seventy-five minutes after administration of the active or control dose, electroconvulsive shock (18 mA, 380 V, 0.1 sec.) was administered, and the animals observed for evidence of seizures. The following results were recorded:

| | Total No. | Without Seizures | Number with Seizures & Severity | | |
|---|---|---|---|---|---|
| | | | 1 | 2 | 3 |
| Water | 19 | 2 | 5 | 9 | 3 |
| 5-Aminopentanoic Acid | 16 | 10 | 3 | 0 | 3 |

The probability that the observed freedom from seizures was due to chance alone was examined using Fisher's Exact Probability test (two-tailed) and it was found that p=0.00328. This is evidence of a statistically valid observation.

TABLE I

Seizure incidence and latency to onset in mice receiving various test agents (subcutaneous administration) 45 min. after administration of L-Methionine-RS-Sulfoximine (MSO, 100 mg/Kg).

Effect of glycine, glycylglycine, and δ-amino-valeric acid (15 mmoles/kg, S.C.) given 45 min. after L-methionine-RS-Sulfoximine (MSO, 100 mg/kg, S.C.). N=total number of animals. Probability of freedom from seizures by chance alone, determined by Fisher's exact probability test (two-tailed): a,=0.0144; b,=0.00787. Significance of the difference in seizure onset time measured by the t-test (two-tailed): c, p<0.0001; d, p<0.003; e, p<0.00005, f, p<0.002.

| Treatment | N | Without Seizures | With Seizures | Latency to Seizure Onset (min.) |
|---|---|---|---|---|
| Saline | 20 | 0 | 20 | 248 ± 7.5 |
| Gly | 4 | 0 | 4 | 158 ± 21.0 c |
| Glygly | 14 | 5 a | 2 | 164 ± 0 d |
| | | | 7 | 354 ± 29.9 e |
| DAVA | 12 | 5 b | 7 | 338 ± 36.5 f |

TABLE II

Effect of various substances on seizure incidence and severity from electro-convulsive seizures (ECS; 18 mA, 380 V, 0.1 sec). 0, No Seizure; 1, Clonic Seizure; 2, Clonic Seizure and Tonic Extension; 3, Death in Tonic Extension. a, Significant by Fisher's Exact Probability test at P=0.00000202; b, P=0.00131; c Severity of Seizures is significantly different from saline controls (chi square analysis), P=0.03; d, Fisher's Exact Probability=0.0108.

| Treatment | Time To ECS | No Seizures (n) 0 | Seizures and Severity (n) | | | Total |
|---|---|---|---|---|---|---|
| | | | 1 | 2 | 3 | |
| Saline | 60 min | 1 | 7 | 15 | 3 | 26 |
| DAVA | 60 min | 17 a | 4 | 4 | 0 | 25 |
| DALA | 60 min | 6 b | 2 | 2 | 0 | 10 |
| GABA | 60 min | 3 | 1 | 5 | 1 | 10 |
| Gly | 60 min | 1 | 0 | 3 | 0 | 4 |
| Glygly | 60 min | 1 | 1 | 3 | 5c | 10 |
| Glygly | 180 min | 6 d | 2 | 1 | 1 | 10 |

TABLE III

Effect of subcutaneous DAVA (15 mmol/kg) on incidence and latency of seizures from pentylenetetrazole (PTX, 65 mg/Kg) administered 60 min later. a, Significant by Fisher;3 s Exact Probability; P=0.0202; b, Significant by t-test at P<0.0001.

| Treatment | No Seizures (n) | Seizures (n) | Latency Time to Seizures (min) |
|---|---|---|---|
| Saline | 0 | 20 | 5.6 ± 0.42 |
| DAVA | 6 a | 14 | 10.7 ± 1.21 b |

DISCUSSION OF TABLES I–III

Glygly had a bimodal effect on the latency of convulsions following MSO (Table 1). The shorter onset time was the same as that seen in the Gly treated animals while the longer latency time was equal to that seen with DAVA. Gln appeared to have no effect on the seizure latency when given 45 min. after MSO. When Gln was injected after seizures had begun, however, it appeared to abort the convulsions for about 30 min. Glygly had no effect on seizures induced by ECS given 60 min. later but was significantly effective with ECS was administered after 180 min. (Table 2). The effect produced by Gly did not differ from that produced by saline at either 60 or 180 minutes. Both DAVA and DALA substantially reduced the convulsive response to electric shock. Seventeen of the 25 animals treated with DAVA and 6 of the 10 mice treated with DALA had no seizure while only one of the 26 saline controls did not have a convulsion (Table 2). The effect of GABA as an anticonvulsant was not statistically significant. In another series of animals, it was observed that 6 of 20 mice receiving DAVA (15 mmol/kg of body weight-subcutaneously) were completely protected against PTZ induced convulsions. The seizure latency time was almost doubled in the remaining 14 animals (Table 3).

EXAMPLE VIII

The following test was performed to illustrate the oral administration of the anticonvulsive agent DAVA. Two groups of mice were given either an aqueous solution containing 30 mmol/kg of body weight of DAVA (buffered to pH 4.5) or an equal volume of distilled water via the oral route. 75 minutes after ingestion of the active or control dose the animals were given electroconvulsive shock using the same apparatus as in Example V (18 MA at 380 V for 0.1 sec.) and observed for seizure behavior.

| Treatment | No. of Animals With Seizures | No Animals Free of Seizures |
|---|---|---|
| Water | 17 | 2 |
| DAVA | 6 | 10 |

Statistical analysis by Fisher's Exact Probability Test of the results yields P=0.00328.

EXAMPLE IX

The following experiment was conducted to compare the anticonvulsant efficacy of the DAVA formulations and methods for administration thereof as taught in the Tsuchiya et al reference and in the present invention.

A DAVA formulation was prepared by dissolving DAVA in Tyrodes solution (buffered to pH 7.4) and administered to a group (I) of six (6) healthy mature adult mice (DBA/2J strain), all as taught in the Tsuchiya et al reference. Each animal was given 1000 mg/kg of body weight of DAVA (by parenteral injection) buffered to pH 7.4 (the maximum dosage administered by Tsuchiya et al as reported in their above-identified article). A separate group (II) of six (6) DBA/2J mice received 763 mg/kg. of body weight of DAVA.HCl (pH 2.0) via the parenteral route.

Ten minutes after administration of the active agent each group of animals (I&II) was given a supramaximal shock using the same technique as Tsuchiya et al supra. The results of the test are set forth in Table IV below. In DBA/2J mice supramaximal shock required application of 20 mA of current at 415 v. for 0.1 sec. through ear electrodes. The results are shown in Table IV below.

TABLE IV

| Group | Dose mg/Kg | Time (Min.) | pH | Route | Total No. Animals | No. With Seizures | No. Without Seizures | % Without Seizures |
|---|---|---|---|---|---|---|---|---|
| I | 1000 | 10 | 7.4 | Parenteral | 6 | 6 | 0 | 0* |
| II | 763 | 10 | 2.0 | Parenteral | 6 | 4 | 2 | 33.3 |

*Procedure of Tsuchiya et al (1960).

The identical procedure was repeated with two further groups (III and IV) of mice, but with the supramaximal shock delivered 60 minutes after administration of the active agent. The results of this test are shown in Table V.

| Group | Dose mg/Kg | Time (Min.) | pH | Route | Total No. Animals | No. With Seizures | No. Without Seizures | % Without Seizures |
|---|---|---|---|---|---|---|---|---|
| III | 1000 | 60 | 7.4 | Parenteral | 6 | 6 | 0 | 0 |
| IV | 670 | 60 | 2.0 | Parenteral | 14 | 5 | 9 | 64.3 |

DISCUSSION OF TABLES IV AND V

The results illustrated in Tables IV and V indicate that administration of DAVA (pH 7.4) ten minutes prior to onset of seizure provoking activity does not provide any seizure prevention. This confirms the report by Tsuchiya et al that DAVA (pH 7.4) administered ten minutes prior to ECS stimuli was ineffective as an anticonvulsant. The administration of DAVA at pH 2.0 with ECS at ten minutes provided anti-convulsant protection to 33.3% of the treated animals. This is not considered to be an effective anticonvulsant, performance level (i.e. To be considered an effective anticonvulsant, an agent must protect at least 50% of the population under treatment against convulsions of this sort). However, administration of DAVA (pH 2.0) sixty minutes prior to application of ECS stimuli protected more than 60% of the population under treatment. The results in Tables IV and V indicate that to achieve effective levels of protection (i.e. greater than 50% of the population protected against seizures), DAVA should be administered at a low pH in the range pH 1.8 to 6.0 (and preferably pH 1.8 to 4.0) and at least 30 minutes prior to the onset of seezures.

It has also been observed that mice injected subcutaneously with 5-aminopentanoic acid or 5-aminolevulinic acid at 15 mmoles/kg behave as if sedated. The animals display considerably less spontaneous movement around the cage than saline injected control mice. When subjected to noxious stimuli (for example, when the ear clips are attached to the mice before ECS is administered, or when nudged with a blunt probe) the 5-aminopentanoic acid or 5-aminolevulinic acid treated mice show less resistive activity. In addition to being a standard test for anti-convulsant activity, protection against pentylenetetrazole seizures is a standard screening procedure for identifying potential anxiolytic agents. The fact that compounds of the present invention (e.g., 5-aminopentanoic acid) are effective against pentylenetetrazole seizures, indicates that these compounds have significant utility as anxiolytic agents. This observation is confirmed by past experience with prior art anticonvulsant agents, which indicates that many of them have dual roles as anxiolytics and sedatives (e.g., diazepam is a sedative, an anxiolytic and an anticonvulsant; phenobarbitol is a sedative, an anxiolytic, and an anticonvulsant). Thus, it is not unusual that the same activity has been identified for the compounds described here.

What is claimed is:

1. A method for controlling seizures in a mammal in need of such treatment which comprises administering to said mammal prior to the onset of a seizure a composition comprising a solid oral dosage form, said oral dosage form containing a pharmaceutical formulation comprising an effective amount for controlling seizures of a member selected from the group consisting of compounds having the general formula $$\begin{array}{c} H \\ \diagdown \\ N-CH-Y-Z_n-CH_2-C \\ \diagup \quad | \quad \quad \quad \quad \quad \diagdown \\ R_1 \quad A \quad \quad \quad \quad \quad R_2 \end{array} \begin{array}{c} O \\ \| \\ \\ \end{array}$$

wherein
$R_1$ is H,

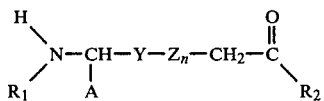

A is H, $CH_3$, $CH_3CH_2$—, $HO\text{-}CH_2$, $HO\text{-}CH_2CH_2$, $CH_3OCH_2$—$HS$—$CH_2$—, $HS$—$CH_2CH_2$—, $CH_3SCH_2$—,
Y is C=O, HC—OH or, CH—A,
Z is CH—A, O, S; and
$R_2$ is —OH,
n is 1, and Y is CH—A when n=0; and
A+Y+Z include no more than one Oxygen or Sulfur atom and acid addition salts of such compounds,
said formulation having a pH between about 1.8 and 6.0.

2. The method of claim 1 which comprises administering a compound wherein n=0 to said mammal.

3. The method of claim 1 which comprises administering a compound wherein n=1 to said mammal.

4. The method as recited in claim 1 which comprises administering said compound substantially before the onset of a seizure.

5. The method of claim 4 wherein said compound is delta aminovaleric acid.

6. The method of claim 4 wherein said compound is delta aminovaleric acid.HCl.

7. The method of claim 4 wherein said compound is delta aminolevulinic acid.

8. The method of claim 4 which comprises administering said compound to said mammal at least 30 minutes prior to the onset of a seizure.

9. The method as recited in claim 6 wherein said pharmaceutical formulation has a pH of about 2.0.

10. The method of claim 4 wherein said oral dosage form is selected from the group consisting of a tablet, a pill, a compressed tablet and a capsule.

11. The method of claim 10 wherein said effective amount comprises from about 3.5 to about 4680 milligrams per kilogram of body weight per day.

12. The method as recited in claim 6 wherein said effective amount comprises from about 50 to about 200 milligrams per kilogram of body weight per day.

13. The method of claim 4 wherein said composition comprises an inert pharmaceutically acceptable carrier in combination with said compound.

14. The method of claim 4 wherein said pharmaceutical formulation comprises an optional acidifying agent to bring the pH of said formulation between about pH 1.8 and pH 6.0.

15. A method of inhibiting epileptic seizures in a patient afflicted with epilepsy which comprises administering to a patient in need of such treatment and prior to the onset of said epileptic seizure a composition comprising a coated solid dosage form, said solid dosage form comprising a pharmaceutical formulation including an effective amount for inhibiting seizures of a member selected from the group consisting of compounds having the general formula

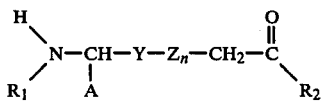

wherein
R$_1$ is H,

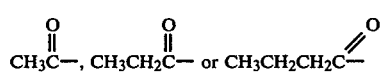

A is H, CH$_3$, CH$_3$CH$_2$—, HO—CH$_2$, HO—CH$_2$CH$_2$, CH$_3$OCH$_2$—HS—CH$_2$—, HS—CH$_2$CH$_2$—, CH$_3$SCH$_2$—,
Y is C=O, HC—OH or, CH—A,
Z is CH—A, O, S; and
R$_2$ is —OH,
n is 1, and Y is CH—A when n=0; and
A+Y+Z include no more than one Oxygen or Sulfur atom and acid addition salts of said compounds,
said formulation having a pH between about pH 1.8 and pH 6.0.

16. A method of sedating a mammal which comprises orally administering to said mammal a composition comprising a coated solid dosage form comprising a pharmaceutical formulation containing a member selected from the group consisting of compounds having the general formula

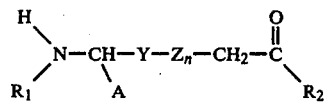

wherein
R$_1$ is H,

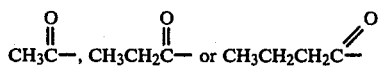

A is H, CH$_3$, CH$_3$CH$_2$—, HO—CH$_2$, HO—CH$_2$CH$_2$, CH$_3$OCH$_2$—HS—CH$_2$—, HS—CH$_2$CH$_2$—, CH$_3$SCH$_2$—,
Y is C=O, HC—OH or, CH—A,
Z is CH—A, O, S; and
R$_2$ is —OH,
n is 1, and Y is CH—A when n=0; and
A+Y+Z include no more than one Oxygen or Sulfur atom, and acid addition salts of said compounds,
and said formulation having a pH in the range pH 1.8 to pH 6.0.

17. A method of tranquilizing a mammal which comprises orally administering to said mammal a composition comprising a coated solid dosage form comprising a pharmaceutical formulation including an effective amount for tranquilizaton of a member selected from the group consisting of compounds of the general formula

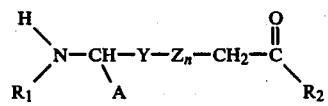

wherein
R$_1$ is H,

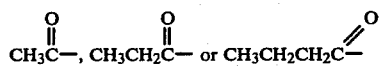

A is H, CH$_3$, CH$_3$CH$_2$—, HO—CH$_2$, HO—CH$_2$CH$_2$, CH$_3$OCH$_2$—HS—CH$_2$—, HS—CH$_2$CH$_2$—, CH$_3$SCH$_2$—,
Y is C=O, HC—OH or, CH—A,
Z is CH—A, O, S; and
R$_2$ is —OH,
n is 1, and Y is CH—A when n=0; and
A+Y+Z include no more than one Oxygen or Sulfur atom and acid addition salts of said compounds,
and said formulation having a pH in the range pH 1.8 to pH 6.0.

18. The method of claim 1 wherein said solid oral dosage form is coated.

19. A composition comprising a solid oral dosage form, containing a pharmaceutical formulation comprising an effective amount for controlling seizures in a mammal of a member selected from the group consisting of compounds having the general formula

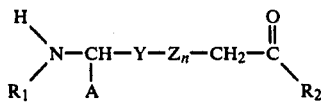

wherein
$R_1$ is H,

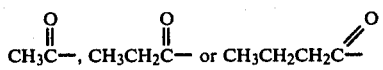

A is H, $CH_3$, $CH_3CH_2-$, $HO-CH_2$, $HO-CH_2CH_2$, $CH_3OCH_2-$ $HS-CH_2-$, $HS-CH_2CH_2-$, $CH_3SCH_2-$,

Y is C=O, HC—OH or, CH—A,

Z is CH—A, O, S; and $R_2$ is —OH, n is 1, and Y is CH—A when n=0.

said formulation having a pH between about pH 1.8 and pH 6.0.

20. The compound of claim 18 wherein n=0.

21. The compound of claim 18 wherein n=1.

22. The compound of claim 20 wherein $R_1$ is hydrogen or acyl, A is hydrogen or methoxy, Y is $CH_2$ or CH—OH and $R_2$ is hydroxy.

23. The compound of claim 21 wherein $R_1$ is hydrogen or acyl, A is hydrogen or methoxy, Y is CH—A, Z is CH—A and $R_2$ is OH.

24. The composition of claim 18 wherein said compound comprises delta aminovaleric acid.

25. The composition of claim 24 wherein said compound comprises an inorganic acid addition salt of delta aminovaleric acid.

26. The pharmaceutical formulation of claim 24 wherein said compound comprises an organic acid addition salt of delta aminovaleric acid.

27. The composition of claim 18 wherein said compound comprises delta aminolevulinic acid.

28. The composition of claim 25 wherein said oral dosage form comprises delta aminovaleric acid.HCl.

29. The composition of claim 24 or 27 wherein said solid form is a member selected from the group consisting of a tablet, a capsule, a pill, a beadlet and a compressed tablet.

30. The composition of claim 24 or 25 comprising an optional pharmaceutically acceptable buffering agent to bring said formulation to between about pH 1.8 and pH 6.0.

31. The pharmaceutical formulation of claim 25 or 26 wherein the pH of said formulation is between about pH 1.8 and pH 4.0.

32. The composition of claim 31 which comprises an inert pharmaceutically acceptable carrier in combination with said compound.

33. The pharmaceutical formulation of claim 25 or 26 wherein the pH of said formulation is between about pH 1.8 and pH 4.0.

34. A composition comprising a rectal suppository containing from about 5 at about 500 milligrams of a member selected from the group consisting of compounds having the general formula

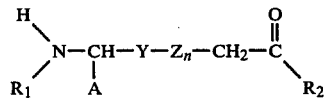

wherein
$R_1$ is H,

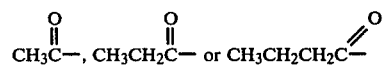

A is H, $CH_3$, $CH_3CH_2-$, $HO-CH_2$, $HO-CH_2CH_2$, $CH_3OCH_2-$ $HS-CH_2-$, $HS-CH_2CH_2-$, $CH_3SCH_2-$,

Y is C=O, HC—OH or, CH—A,

Z is CH—A, O, S; and $R_2$ is —OH, n is 1, and Y is CH—A when n=0; and

A+Y+Z include no more than one Oxygen or Sulfur atom, and acid addition salts of such compounds said composition having a pH between about pH 1.8 and 6.0, in a shapable base material having a melting point that will enable said suppository to melt slowly upon retention in the rectal cavity.

35. The composition as described in a claim 34 wherein said compound is delta-aminovaleric acid.

36. The composition as described in claim 34 wherein said compound is delta-aminolevulinic acid.

37. The composition of claim 27 wherein said solid is in a suspension.

38. The composition of claim 19 comprising a coated solid oral dosage form.

* * * * *

REEXAMINATION CERTIFICATE (418th)

United States Patent [19]
Fish et al.

[11] B1 4,372,974
[45] Certificate Issued * Nov. 12, 1985

[54] ANTICONVULSIVE COMPOSITIONS AND METHOD OF TREATING CONVULSIVE DISORDERS

[75] Inventors: Irving Fish, Tenafly, N.J.; Stephen A. Schwartz, Bronx; Stanley Samuels, White Plains, both of N.Y.

[73] Assignee: New York University, New York, N.Y.

Reexamination Request:
No. 90/000,508, Feb. 21, 1984

Reexamination Certificate for:
Patent No.: 4,372,974
Issued: Feb. 8, 1983
Appl. No.: 269,629
Filed: Jun. 2, 1981

[*] Notice: The portion of the term of this patent subsequent to Mar. 30, 1999 has been disclaimed.

[63] Continuation-in-part of Ser. No. 162,907, Jun. 25, 1980, Pat. No. 4,322,440.

[51] Int. Cl.$^4$ .............................................. A61K 31/195
[52] U.S. Cl. ................................... 514/561; 514/562; 514/563
[58] Field of Search ......................................... 424/319

[56] References Cited

U.S. PATENT DOCUMENTS 3,629,451  12/1971  Cook et al. ........................ 514/561

*Primary Examiner*—Stanley J. Friedman

[57] ABSTRACT

An orally administered pharmaceutical formulation comprising a solid dosage form containing an aliphatic amino acid compound in which the carboxylic acid and primary amine are separated by three or four units. Administered in an acid pH range, the formulation is useful in the treatment of convulsive disorders and also has anxiolytic and sedative properties.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–9 and 12–18 is confirmed.

Claims 19–38 are cancelled.

Claim 10 is determined to be patentable as amended.

Claim 11, dependent on an amended claim, is determined to be patentable.

10. The method of claim 4 wherein said oral dosage form is selected from the group consisting of a tablet, a pill, a compressed tablet and a capsule *said composition also comprising on inert pharmaceutically acceptable carrier.*

* * * * *